(12) United States Patent
Squirrell et al.

(10) Patent No.: US 7,648,830 B2
(45) Date of Patent: Jan. 19, 2010

(54) METHOD FOR DETERMINING THE PRESENCE OF BACTERIA RESISTANT TO CELL LYSING ANTIBIOTICS

(75) Inventors: David James Squirrell, Salisbury (GB); Rachel Louise Leslie, Salisbury (GB); Kevin J Bown, Salisbury (GB)

(73) Assignee: The Secretary of State for Defence in Her Britannic Majesty's Government of the United Kingdom of Great Britain and Northern Ireland, Salisbury, Wiltshire (GB)

( * ) Notice: Subject to any disclaimer, the term of this patent is extended or adjusted under 35 U.S.C. 154(b) by 202 days.

(21) Appl. No.: 10/490,229

(22) PCT Filed: Sep. 2, 2002

(86) PCT No.: PCT/GB02/03990

§ 371 (c)(1),
(2), (4) Date: Mar. 19, 2004

(87) PCT Pub. No.: WO03/025208

PCT Pub. Date: Mar. 27, 2003

(65) Prior Publication Data

US 2004/0248199 A1  Dec. 9, 2004

(30) Foreign Application Priority Data

Sep. 21, 2001  (GB)  ................. 0122790.9

(51) Int. Cl.
  C12Q 1/18  (2006.01)
  C12Q 1/14  (2006.01)
  G01N 33/569  (2006.01)
  C12P 1/00  (2006.01)
  C12P 37/00  (2006.01)
  A61K 39/085  (2006.01)
  A61K 39/40  (2006.01)
  A61K 39/09  (2006.01)
  A01N 63/00  (2006.01)

(52) U.S. Cl. .............. 435/32; 435/7.33; 435/36; 435/41; 435/43; 424/243.1; 424/165.1; 424/237.1; 424/93.42

(58) Field of Classification Search ............... 435/7.33, 435/7.32, 883, 36, 41, 43, 968; 530/388.4; 424/7.33, 243.1, 165.1, 237.1, 93.42
See application file for complete search history.

(56) References Cited

U.S. PATENT DOCUMENTS

| 4,647,536 | A |   | 3/1987  | Mosbach et al. |
|-----------|---|---|---------|----------------|
| 5,496,706 | A | * | 3/1996  | Kuusela et al. ............. 435/7.33 |
| 5,695,946 | A |   | 12/1997 | Benjamin et al. |
| 5,776,712 | A | * | 7/1998  | Kuusela et al. ............. 435/7.33 |
| 5,798,214 | A |   | 8/1998  | Squirrell |
| 6,156,524 | A |   | 12/2000 | Fournier et al. |
| 2006/0073530 | A1 | * | 4/2006 | Schneewind et al. ........ 435/7.32 |

FOREIGN PATENT DOCUMENTS

| EP | 0 441 469 A1 |   | 8/1991 |
|----|--------------|---|--------|
| GB | WO 99/37799  | * | 7/1999 |
| GB | WO99/37799   | * | 7/1999 |
| JP | 11028099     |   | 2/1999 |
| WO | WO 94/17202  |   | 8/1994 |
| WO | WO 95/14105  |   | 5/1995 |
| WO | WO 95/16039  |   | 6/1995 |
| WO | WO 96/02665  |   | 2/1996 |
| WO | WO 99/37799  |   | 7/1999 |
| WO | WO 99/50441  |   | 10/1999 |

OTHER PUBLICATIONS

Bacteriophage Definition—Stedman's Medical Dicitionary.*
Bacteriophage Definition—Stedman's Medical Dicitionary, May 2005.*
Stranden, et al., "Cell Wall Monoglycine Cross-Bridges and Methicillin Hypersusceptitility in a *femAB* Null Mutant of Methicillin-Resistant *Staphylococcus aureus*," Journal of Bacteriology, 179(1):9-16 (1997).

* cited by examiner

Primary Examiner—Robert B Mondesi
Assistant Examiner—Lakia J Tongue
(74) Attorney, Agent, or Firm—Kilpatrick Stockton LLP

(57) ABSTRACT

A method is provided for determining the presence of a target bacteria based on its resistance to a cell lysing antibiotic. Said antibiotic is used to lyse cells of non-target bacteria in a sample and hence facilitate isolation of the target prior to detection by known means.

16 Claims, 3 Drawing Sheets

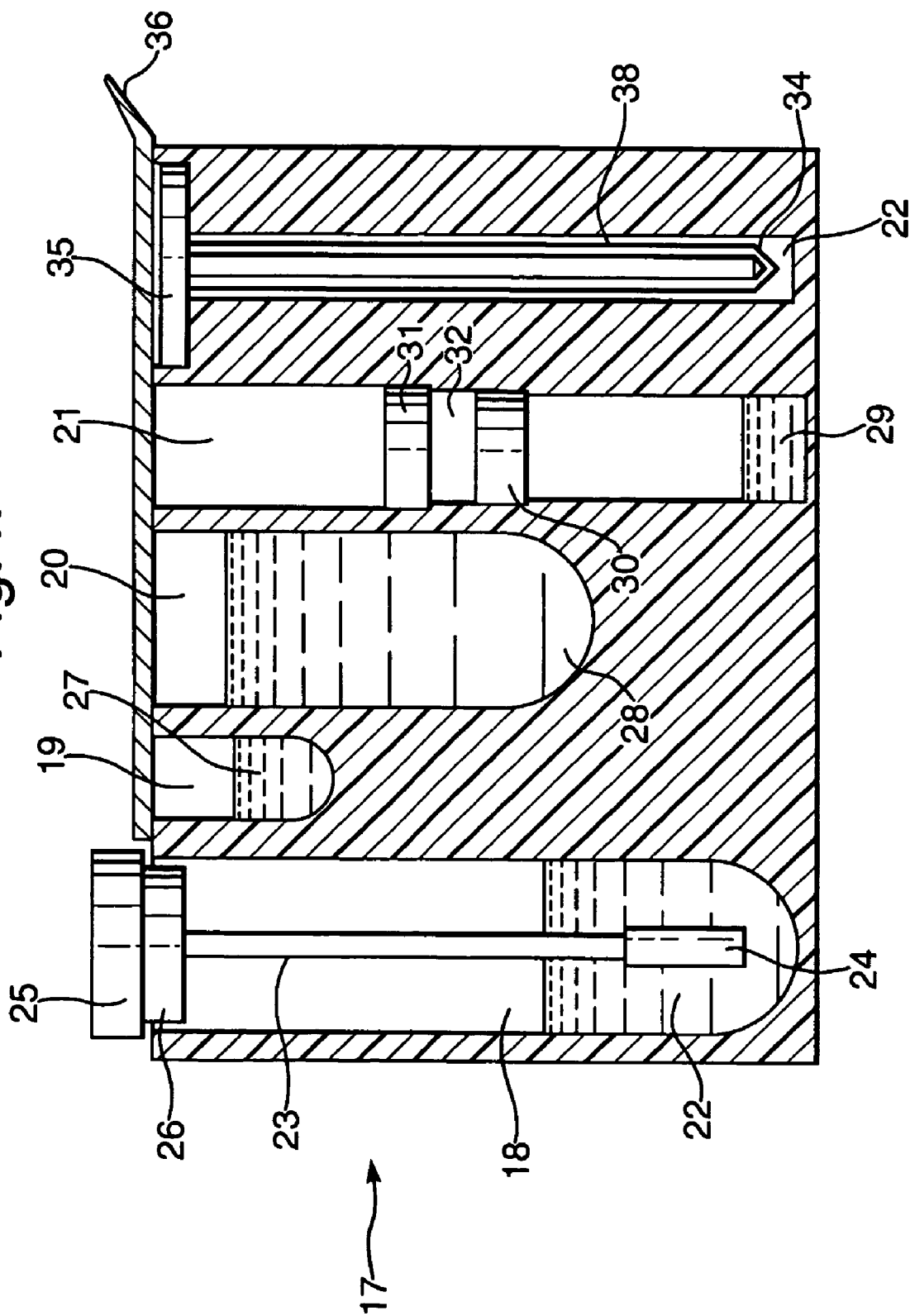

METHOD FOR DETERMINING THE PRESENCE OF BACTERIA RESISTANT TO CELL LYSING ANTIBIOTICS

CROSS REFERENCE TO RELATED APPLICATIONS

This application is the U.S. national phase of International Application No. PCT/GB02/03990 filed on Sep. 2, 2002 and published in English as International Publication No. WO 03/025208 A1 on Mar. 27, 2003, which application claims priority to Great Britain Application No. 0122790.9 filed on Sep. 21, 2001, the contents of which are incorporated by reference herein.

The present invention is directed to a method for determining the presence of one or more target bacteria in a sample, which target bacteria are resistant to a cell-lysing antibiotic or antibiotics. The invention is particularly, although not exclusively, directed to a method for determining the presence of one or more methicillin-resistant bacteria in a clinical sample.

The emergence of bacteria having resistance to commonly used antibiotics is an increasingly prevalent problem with serious implications for the treatment of infected individuals. Indeed, these so-called superbugs, such as *Staphylococcus aureus*, are often resistant to all but the most powerful antibiotics. The problem has become particularly acute in the hospital environment where nosocomial infection of individuals with weakened immune systems by bacteria resistant to antibiotics can lead to severe complications and even death. Consequently, there is a need to minimise the risk of infection in such an environment. One way of minimising the risk relies on the early determination of the presence of such bacteria so as to enable individuals and an environment to be carefully monitored and, if necessary, treated at an early stage.

Present methods for the determination of the presence of bacteria resistant to antibiotics are, however, time consuming and require that the bacteria first be cultured in pure form and then exposed to a set of antibiotics to see whether their growth is inhibited. The whole process can take at least two days and can result in an often, critical delay before an optimum treatment regimen can be administered to an infected individual. Of course, such delays are not only deleterious to the health of individuals but also result in longer stays in the hospital environment.

Consequently, there is a need for a method for the rapid determination of the presence of bacteria which are resistant to certain antibiotics in a patient or environment.

WO 99/37799, Applicant's co-pending application, teaches a rapid method for determining whether a particular bacterium, known to be present in a culture, is susceptible or resistant to a particular antibiotic. The method is, however, limited in that it preferably requires that the bacterium is present as a pure culture or is a pure isolate. The method, however, can be adapted for determining the antibiotic resistance or susceptibility of a particular bacterium in a mixed culture. In that case the method generally relies on a preliminary separation step prior to treatment with the particular antibiotic or other action specific for the particular bacterium.

Alternatively, and provided the mode of action of the antibiotic is known, the method can reveal the antibiotic resistance or susceptibility of a particular bacterium known to be present in a mixed culture through a comparative analysis of the intracellular adenylate kinase content of four aliquots derived from the mixed culture and cultured in the presence of i) no antibiotic ii) antibiotic, iii) a bacteriophage specific to the bacterium and iv) a mixture of both the antibiotic and the bacteriophage. A bacterium susceptible to a cell-lysing antibiotic, for example, may be deduced on the basis that intracellular adenylate kinase is reduced in the sample cultured with the antibiotic and bacteriophage when compared with the sample cultured with the bacteriophage alone.

Although it might be supposed that the methods disclosed in WO 99/37799 might simply indicate the presence of bacterium in a mixed culture having resistance to a particular antibiotic, in practice such a result cannot be unambiguously and reliably obtained especially where concentrations of resistant bacteria are low.

Even, if it could, it will be apparent that the determination of that presence still requires the performance of a number of repetitive steps involving the culture, treatment and assay of at least four different aliquots from the mixed culture. Such repetitions are inelegant and increase the possibility of error. Further, the method comprises an inherent delay in that the treatment of an aliquot of the mixed culture with a bacteriophage requires time to ensure that the bacteria are established in the log phase of their growth.

Consequently, there remains a need for a simple, rapid method for determining the presence of bacteria having antibiotic resistance in a sample. In particular, there remains a need for a simple, and rapid method for determining the presence of bacteria having antibiotic resistance in a clinical sample.

The present invention therefore seeks to provide a simple and rapid method, involving a minimum of necessary steps, for determining whether antibiotic resistant bacteria are present in a sample, especially a clinical sample, taken, for example, by swabbing infected individuals.

The present invention starts from the realisation that a wide range of bacteria are generally susceptible to cell lysing antibiotics and that, in consequence, the intracellular material of susceptible bacteria in a mixed culture can be advantageously discarded in the first instance.

Accordingly, the present invention provides a method for determining the presence of target bacteria in a sample, which target bacteria are resistant to a cell lysing antibiotic, comprising the sequential steps of:
i) incubating the sample in an incubating medium including the cell lysing antibiotic,
ii) capturing unlysed cells of the target bacteria on a solid support comprising a capture agent,
iii) exposing the unlysed cells of the target bacteria to an agent capable of causing cell lysis thereof,
iv) determining the presence of intracellular material from the lysed cells of the target bacteria.

In one embodiment of the present invention the method further comprises a washing step and/or a filtration step preceding step iii), so as to remove intracellular and material derived from cells susceptible to the cell lysing antibiotic.

It will be understood that throughout this application the phrase "cell lysing antibiotic" describes an agent which disrupts bacterial cell wall synthesis during cell replication. Thus, any of the β-lactam antibiotics are suitable for the performance of the method of the present invention. In a preferred embodiment of the present invention the cell lysing antibiotic is a penicillin such as ampicillin or methicillin.

In one embodiment of the present invention the capture agent may be specific only to a particular species of bacteria. In other embodiments the capture agent may be specific to a particular strain of bacteria. In a preferred embodiment the capture agent is fibrinogen which binds to *Staphylococcus aureus*. Alternatively the capture agent is an antibody specific to *Staphylococcus aureus*.

It will of course be realised that the method of the present invention may include an additional intervening step or steps so as to enable the presence of more than one target bacteria to be determined. Typically, these steps may comprise capturing unlysed cells of the target bacteria on a solid support comprising one or more capture agents.

Advantageously, the culture medium for performing the present invention comprises a liquid broth. In this embodiment the solid support may comprise magnetic beads coated with a suitable antibody or other capture agent. Alternatively, the solid support may comprise a spatula, paddle or filter at least in part coated with a suitable antibody or other capture agent.

In a further embodiment of the present invention the agent capable of causing cell lysis is selective towards the target bacteria. Preferably the agent is selective to *Staphylococcus aureus*. Still more preferably the agent capable of causing cell lysis is lysostaphin.

In another embodiment of the present invention, the agent capable of causing cell lysis is a bacteriophage selective to the target bacteria or a lysin derived therefrom. In a further embodiment the agent capable of causing cell lysis is a colicin.

Of course it will also be realised that the method of the present invention may include a number of such steps so that the presence of other target bacteria may be also determined.

The determination of intracellular material derived from lysed cells of the target bacteria may comprise any appropriate assay as is known to the art. Preferably, the assay comprises a bioluminesence assay. Still more preferably, the bioluminescence assay is based on adenylate kinase (AK) as is described, for example, in Applicant's co-pending applications WO 94/17202 and WO 96/02665. However, the assay may alternatively comprise a colorimetric or fluorimetric assay based on intracellular enzyme markers—for example, phosphatase or peroxidase.

One aspect of the present invention provides for test kits for performing the method of the invention. Preferably, the test kit is a disposable test kit. The test kit may comprise suitable components so as to allow the chosen assay to be carried out. Preferably, the test kit comprises a suitable culture medium containing a chosen cell lysing antibiotic. Still more preferably, the test kit comprises a solid support including a capture agent specific to the target bacteria, a wash solution and an agent capable of causing cell lysis of the target bacteria.

In one embodiment of the present invention, the test kit comprises a liquid broth comprising methicillin. Preferably, the liquid broth containing methicillin is supplied in a freeze-dried form.

Advantageously, the test kit may be supplied in the form of a multi-well container such as that described in Applicant's co-pending patent application GB 0110476.9.

One advantage of the method of the present invention provides a rapid (about 3 hours) determination for the presence of bacteria resistant to a cell lysing antibiotic involving a single assay for intracellular material. In addition, the method avoids the need for multiple, comparative assays and further confers the advantage that the results may be interpreted in an unambiguous, independently qualitative way, rather than in a comparative or quantitative way.

BRIEF DESCRIPTION OF THE FIGURES

The present invention will now be described by reference to non-limitative embodiments and the following drawings in which

FIG. 4 is a section view of a test kit according to the present invention.

Referring now to FIG. 1, a sample taken in the form of a swab, for example from a patient, and comprising a mixture of bacteria containing, generally methicillin resistant, bacteria 11 and, generally susceptible bacteria 12, is cultured at 37° C. in a liquid broth of about 1 ml volume containing about 4 µg of the antibiotic.

Figure 1:
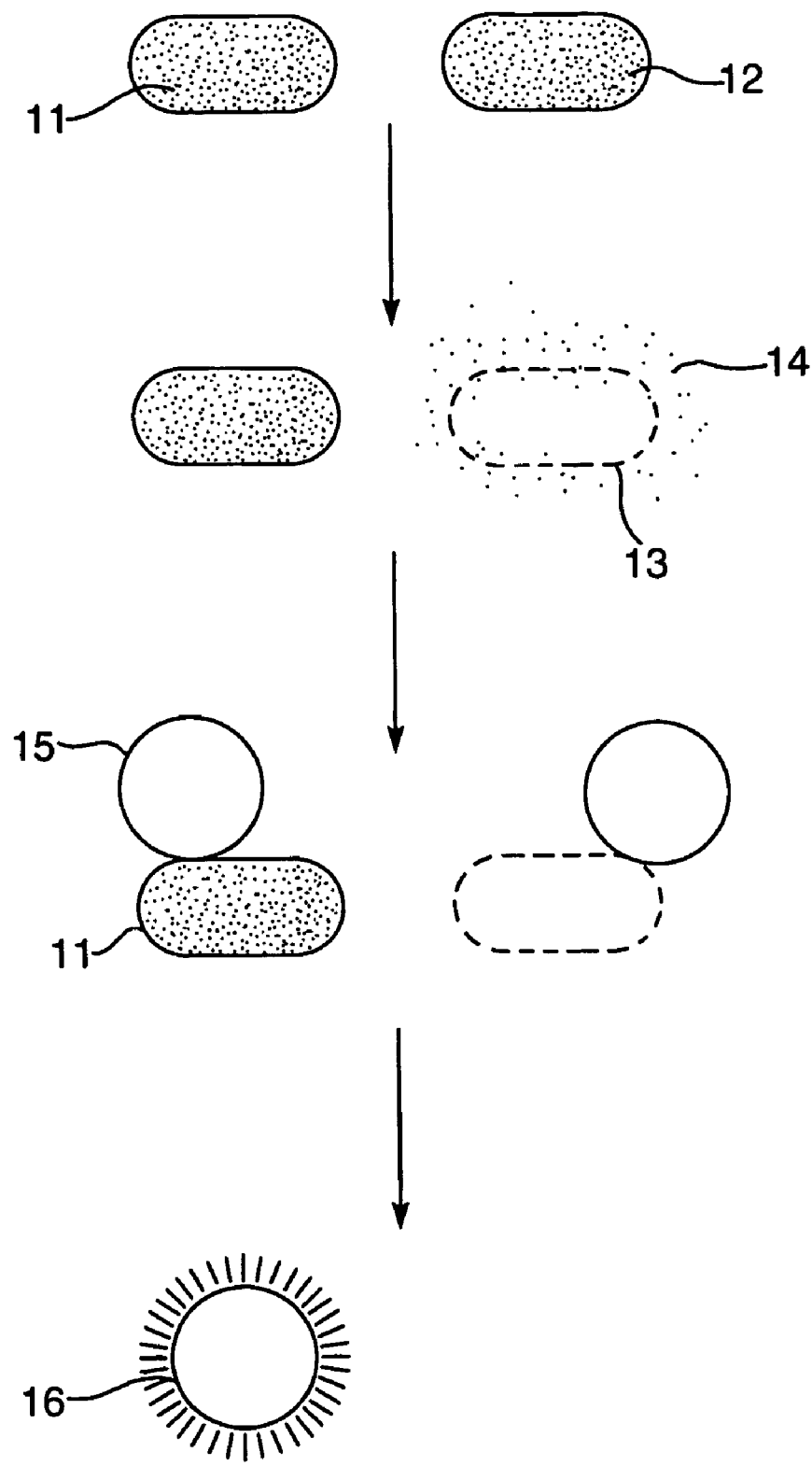
FIG. 1 is a schematic illustration of the essential steps of the method of the present invention.

Bacteria resistant to methicillin 11 survive and may multiply. Bacteria susceptible to methicillin 12, however, after an initial growth phase, develop weakened cell walls 13 and lyse, releasing their intracellular material 14 to the liquid broth.

After a period of 2 to 4 hours the liquid broth therefore comprises a mixture of methicillin-resistant, non-lysed bacteria and methicillin-susceptible lysed bacteria.

The presence of the particular bacteria, *Staphylococcus aureus* for example, is then determined by the addition to the liquid broth of paramagnetic beads 15 coated with fibrinogen. Fibrinogen is a specific binding agent for *Staphylococcus aureus*. After a period of 2 to 10 minutes the beads are magnetically removed from the broth and washed prior to an analysis step.

The beads 15 and the attached target bacteria 11 are then treated in a separate vessel with a detergent capable of lysing the cells. The intracellular material thus obtained is analysed for adenylate kinase using a luciferin-luciferase bioluminescence protocol. The presence of methicillin resistant *Staphylococcus aureus* is revealed by a signal 16. The signal 16 may, for the purposes of certainty, be compared to a suitable control signal so as to exclude anomalies arising from background concentrations of adenylate kinase.

It will be apparent that only those cells which remain impervious to methicillin and are immobilised on the magnetic beads provide a significant signal in response to the adenylate kinase assay.

Of course, the presence of other methicillin resistant target species may be investigated by an alternative or additional step or steps comprising the addition of beads comprising other coatings or beads including one or more capture agents in their coatings.

Alternatively or additionally specificity can be introduced into the method by targeting a particular variety of the bacterial species in the final cell lysis step. For example, a bacteriophage or a detergent combination which is specific to *Staphylococcus aureus* may be used.

Figure 2:
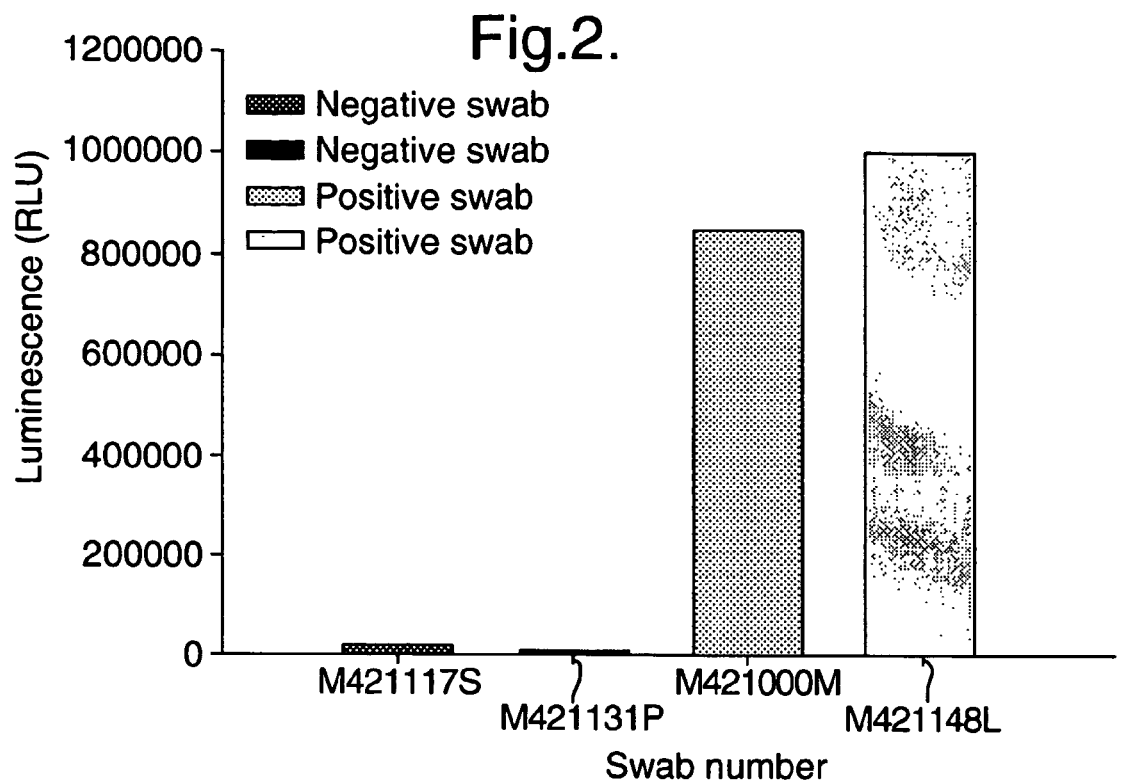
FIG. 2 is a graph highlighting the difference between negative and positive tests.

FIG. 2 shows the bioluminescence results obtained for the determination of the presence of *Staphylococcus aureus* in a series of clinical samples. As may be seen a positive test result (sample numbers M421000M and M421148L) is readily distinguished from a negative test result (sample numbers M421117S and M421131P).

Figure 3:
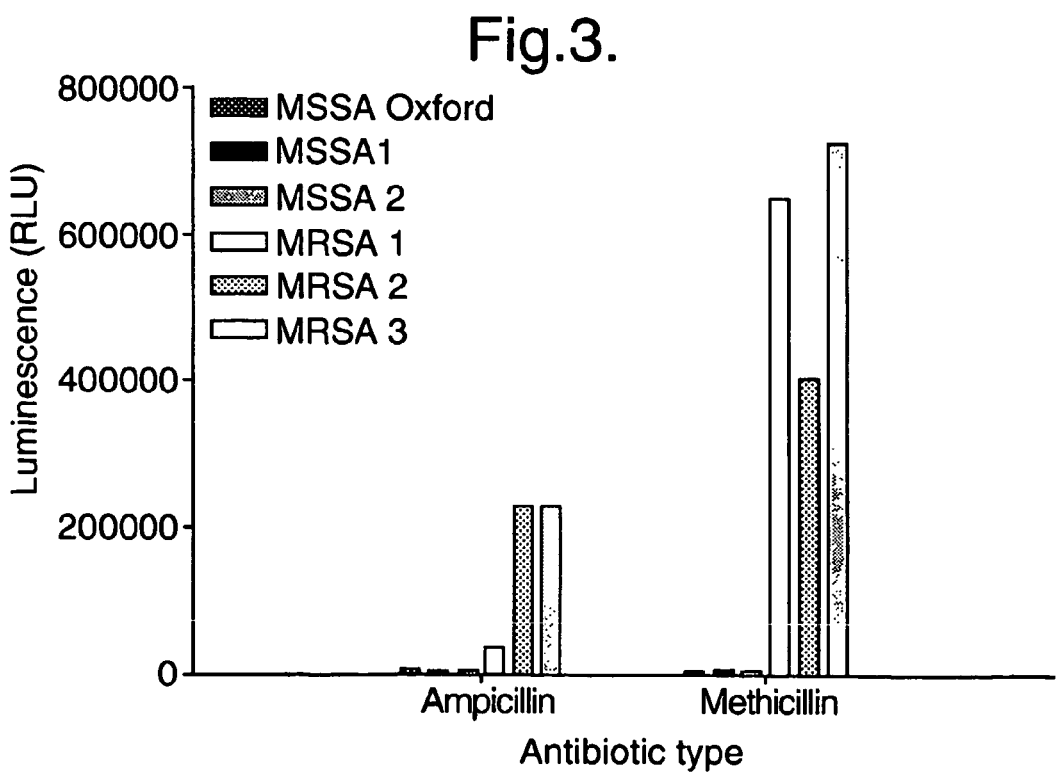
FIG. 3 is a graph showing test results on methicillin-resistant and methicillin-sensitive strains of *Staphylococcus aureus* after an 3.5 h incubation with 50 µg/ml of ampicillin or 4 µg/ml methicillin.

FIG. 3 shows the bioluminescence results obtained for different strains of *Staphylococcus aureus* cultured in the presence of ampicillin as well as methicillin. In each case the method distinguishes the presence of antibiotic resistant strains from antibiotic susceptible strains.

Referring now to FIG. 4, a test kit for use in the method of the present invention comprises a solid, injection moulded polypropylene housing, generally designated 17, comprising a number of wells 18, 19, 20, 21, 22 which act as storage chambers and/or reaction chambers for various suitable tools or reagents (as are described below).

Chamber 18 stores a liquid broth 22 containing a cell lysing antibiotic which is suitable for incubating a swab sample obtained from an infected individual. The chamber 18 is provided with a solid rod 23 carrying a swab 24 for obtaining this sample. Rod 23 carries a transverse portion 25 which acts as a handle for rod 18 and conveniently provides a lid 26 sealing the liquid broth 22 containing the cell lysing antibiotic in chamber 18.

Adjacent chambers 19, 20 respectively store an aqueous solution containing a suspension of magnetic beads 27 and an aqueous, phosphate buffered, saline, wash solution 28. Suitable magnetic beads are those obtained from Dynal under the name Dynabeads™. As mentioned previously the beads are coated with an agent capable of capturing the target bacteria.

Chamber 21, which acts as the reaction chamber of the kit, is provided with an aqueous, buffer solution 29 suitable for performance of a bioluminescence assay based on adenylate kinase. The chamber is also provided with foil sealed capsules 30, 31 above the buffer solution 29 containing respectively a luciferin/luciferase based bioluminescent reagent and an aqueous solution of adenosine diphosphate containing a detergent or agent capable of lysing cells of the target bacteria. A source of magnesium, such as magnesium acetate, which acts as a promoter for bioluminescence assay, is provided in the space 32 dividing the foil sealed capsules.

Chamber 22 is provided with a hollow wand 33 which carries a sharp conical tip 34 suitable for piercing the foil sealed capsules 30, 31. Wand 33 is provided with a transverse portion 35 carrying engagement means (eg. slots—not shown) for engaging a mechanism suitable for moving the wand 33 in vertical and horizontal directions under the control of control hardware or software (not shown). Transverse portion 35 is also provided with an aperture (not shown) allowing the wand 33 to receive a retractable cylindrical magnet (not shown).

Chambers 19, 20, 21, 22 are provided with laminate sealing means in the form a metal foil 36. In contrast to the sealing means provided to chamber 18, the laminate sealing means is not intended to be re-usable after it has been broken.

In use, the solid rod 23 carrying swab 24 is manually removed from chamber 18 by the handle 25 and used to obtain a sample from an infected individual. The rod 23 is immediately returned to the chamber so that the swab 24 is immersed in the liquid broth 22 and the seal between the lid 26 and the chamber 18 is reformed.

The test kit is held under suitable conditions for a period of about 3 h so as to incubate the patient sample. At the end of this period rod 23 is removed from chamber 18 and the metal foil sealing chambers 19, 20, 21, 22 removed.

The hollow wand 33 (containing the retractable magnet) is engaged with the moving mechanism. Under the control of the hardware or software control wand 33 is moved to chamber 19 where it collects the magnetic beads from suspension 27 and thence to chamber 18 where retraction of the magnet by, for example worm drive means, causes the beads to be deposited in the broth.

After a suitable period, and if appropriate stirring, the magnet is returned to the wand 33 so that it collects the beads. Wand 33 is then removed to chamber 20 where the beads are deposited in the wash solution 28 and after a further suitable period retrieved as previously described.

Wand 33 carrying the washed beads is subsequently removed to the reaction chamber 21 so that the sharp, conical tip 34 is caused to release the contents of foil sealed capsules 30, 31 to the buffer solution 29. The beads are then released to the solution 29 by retraction of the magnet from wand 33 and the wand returned to chamber 22.

A photomultiplier (not shown) placed beneath the chamber 21 of polypropylene housing 17 detects the emitted light from the bioluminescence reaction that follows. (A detailed description of the reaction is given in Applicant's co-pending applications WO 94/17202 and WO 96/02665).

The invention claimed is:

1. A method for determining the presence of antibiotic-resistant bacteria in a biological sample, wherein cells of the antibiotic-resistant bacteria are resistant to a cell lysing antibiotic, comprising the sequential steps of:
   (i) incubating the sample in an incubating medium including the cell lysing antibiotic, wherein the cell lysing antibiotic lyses cells of bacteria in the sample that are not resistant to lysis by the cell lysing antibiotic and the lysed cells release intracellular material, and wherein the cell lysing antibiotic does not lyse cells of the antibiotic-resistant bacteria in the sample that are resistant to lysis by the cell lysing antibiotic, wherein the antibiotic-resistant bacteria is *Staphylococcus aureus*:
   (ii) immobilizing the unlysed cells of the antibiotic-resistant bacteria on a solid support,
   (iii) separating and removing the intracellular material from said support upon which the immobilized cells are attached,
   (iv) exposing the unlysed cells of the antibiotic-resistant bacteria to a cell lysing agent that is different from the cell lysing antibiotic in step (i), wherein the agent lyses the cells of the antibiotic-resistant bacteria and the lysed cells release intracellular material, and
   (v) detecting the intracellular material released from the lysed cells of the antibiotic-resistant bacteria, wherein detection of the intracellular material released from the lysed cells of the target antibiotic-resistant bacteria indicates the presence in the sample of bacteria resistant to the cell lysing antibiotic.

2. The method of claim 1, wherein step (iv) is preceded by a washing step.

3. The method of claim 1, wherein the unlysed cells of the antibiotic-resistant bacteria are immobilized on the solid support by an antibody specific to *Staphylococcus aureus*.

4. The method of claim 1, wherein the unlysed cells of the antibiotic-resistant bacteria are immobilized on the solid support by fibrinogen.

5. The method of claim 1, wherein the cell lysing agent is lysostaphin.

6. The method of claim 1, wherein the cell lysing agent is a bacteriophage.

7. The method of claim 1, wherein the incubating medium is a liquid broth.

8. The method of claim 1, wherein the solid support comprises magnetic beads.

9. The method of claim 2, wherein intracellular material released from the lysed cells of the antibiotic-resistant bacteria is detected by a bioluminescence assay.

10. The method of claim 9, wherein the bioluminescence assay is based on adenylate kinase.

11. The method of claim 2, wherein intracellular material released from the lysed cells of the antibiotic-resistant bacteria is detected by a colorimetric or fluorimetric assay based on an intracellular enzyme marker.

12. The method of claim 1, wherein the cell lysing antibiotic is methicillin.

13. The method of claim 1, wherein the cell lysing antibiotic is a beta-lactam antibiotic.

14. The method of claim 1, wherein the cell lysing antibiotic is a penicillin.

15. The method of claim 1 wherein step (iii) is a filtration step.

16. The method of claim 1, wherein the cell lysing antibiotic is ampicillin.

* * * * *